US00PP14122P29

(12) United States Plant Patent
McDonald

(10) Patent No.: US PP14,122 P2
(45) Date of Patent: Sep. 2, 2003

(54) ARGYRANTHEMUM PLANT NAMED 'SUPAMARG'

(75) Inventor: Daniel Bede McDonald, Seven Hills (AU)

(73) Assignee: NuFlora International Pty. Ltd., New South Wales (NL)

( * ) Notice: Subject to any disclaimer, the term of this patent is extended or adjusted under 35 U.S.C. 154(b) by 0 days.

(21) Appl. No.: 10/171,847

(22) Filed: Jun. 17, 2002

(51) Int. Cl.[7] ..... A01H 5/00
(52) U.S. Cl. ..... Plt./263

(58) Field of Search ..... Plt./263

*Primary Examiner*—Bruce R. Campell
*Assistant Examiner*—Anne Marie Grünberg
(74) *Attorney, Agent, or Firm*—C. A. Whealy

(57) ABSTRACT

A distinct cultivar of Argyranthemum plant named 'Supamarg', characterized by its compact, uniform, upright to outwardly spreading, and mounded plant habit; freely branching habit, dense and bushy plants; glossy dark green foliage; freely flowering habit with numerous inflorescences per plant; single inflorescence form; pink and white bi-colored ray florets and disc florets that are initially dark red at the apex and become bright yellow with development.

1 Drawing Sheet

Botanical classification/cultivar denomination: *Argyranthemum frutescens* cultivar Supamarg.

BACKGROUND OF THE INVENTION

The present invention relates to a new and distinct cultivar of Argyranthemum plant, botanically known as *Argyranthemum frutescens* and hereinafter referred to by the name 'Supamarg'.

The new Argyranthemum is a product of a planned breeding program conducted by the Inventor in Cobbitty, New South Wales, Australia. The objective of the program is to create and develop new compact Argyranthemum cultivars with numerous inflorescences with attractive ray floret coloration.

The new Argyranthemum originated from a cross by the Inventor in 1998 of a proprietary selection of *Argyranthemum frutescens* identified as code number X96.1999.1, not patented, as the female, or seed, parent with a proprietary selection of *Argyranthemum frutescens* identified as code number J25, not patented, as the male, or pollen, parent. The new Argyranthemum was discovered and selected by the Inventor as a plant within the progeny of the stated cross in a controlled environment in Cobbitty, New South Wales, Australia in October, 1999. The selection of the new Argyranthemum was based on its numerous single inflorescences and pink and white bi-colored ray florets.

Asexual reproduction of the new Argyranthemum by terminal cuttings taken in a controlled environment in Cobbitty, New South Wales, Australia, since October, 1999, has shown that the unique features of this new Argyranthemum are stable and reproduced true to type in successive generations.

SUMMARY OF THE INVENTION

The new Argyranthemum has not been observed under all possible environmental conditions. The phenotype may vary somewhat with variations in environment such as temperature and light intensity without, however, any variance in genotype.

The following characteristics have been repeatedly observed and are determined to be basic characteristics of 'Supamarg' and distinguish the new Argyranthemum as a new and distinct cultivar:

1. Compact, uniform, upright to outwardly spreading, and mounded plant habit.
2. Freely branching habit, dense and bushy plants.
3. Glossy dark green foliage.
4. Freely flowering habit with numerous inflorescences per plant.
5. Single inflorescence form.
6. Pink and white bi-colored ray florets and disc florets that are initially dark red at the apex and become bright yellow with development.

Plants of the new Argyranthemum differ from plants of the female parent, the X96.1999.1, in the following characteristics:

1. Plants of the new Argyranthemum are more compact than plants of the selection X96.1999.1.
2. Plants of the new Argyranthemum have pink and white bi-colored ray florets whereas plants of the selection X96.1999.1 have cream-colored ray florets.

Plants of the new Argyranthemum differ from plants of the male parent, the selection J25, primarily in ray floret coloration as plants of the selection J25 have pink-colored ray florets.

Plants of the new Argyranthemum can be compared to plants of the cultivar Cobsing, not patented. In side-by-side comparisons conducted in Encinitas, Calif., plants of the new Argyranthemum differed from plants of the cultivar Cobsing in the following characteristics:

1. Plants of the new Argyranthemum were more vigorous and not as compact as plants of the cultivar Cobsing.
2. Plants of the new Argyranthemum were not as freely branching as plants of the cultivar Cobsing.
3. Plants of the new Argyranthemum flowered later than plants of the cultivar Cobsing.
4. Ray florets of plants of the new Argyranthemum were pink and white bi-colored whereas ray florets of plants of the cultivar Cobsing were pink in color.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which accurately describe the colors of the new Argyranthemum.

The photograph at the top of the sheet comprises a side perspective view of three typical flowering plants of 'Supamarg' grown in a 21-5-cm container. The photograph at the bottom of the sheet comprises a close-up view of typical leaves, flower buds and inflorescences of 'Supamarg'.

DETAILED BOTANICAL DESCRIPTION

The aforementioned photographs, following observations and averaged measurements describe plants grown in Encinitas, Calif., in an outdoor nursery during the late winter and early spring with day temperatures about 15° to 24° C., night temperatures about 10° to 19° C., and light levels about 5,000 foot-candles. Plants were grown for 14 weeks in 21.5-cm containers with three plants per container. Plants were pinched one time about five weeks after planting. Color references are made to The Royal Horticultural Society Colour Chart except where general terms of ordinary dictionary significance are used.

Botanical classification: *Agyranthemum frutescens* cultivar Supamarg.

Parentage:

*Female or seed parent.*—Proprietary selection of *Argyranthemum frutescens* identified as code number X96.1999.1, not patented.

*Male or pollen parent.*—Proprietary selection of *Argyranthemum frutescens* identified as code number J25, not patented.

Propagation:

*Type.*—Terminal vegetative cuttings.

*Time to initiate roots.*—About 10 days at 20° C.

*Time to produce a rooted cutting.*—About 21 days at 20° C.

*Root description.*—Fine, fibrous and freely branching.

Plant description:

*General appearance.*—Inverted triangle; compact, uniform, upright to outwardly spreading, and mounded plant form with dense foliage and inflorescences held above the foliage on long peduncles. Vigorous growth habit.

*Plant height.*—About 38 cm.

*Plant width.*—All three plants: About 74 cm. Single plant: About 35 cm.

*Lateral branch description.*—Quantity per plant: About 9. Length: About 34 cm. Width: About 6 mm. Internode length: About 1 cm. Aspect: Upright to outward. Texture: Smooth, glabrous. Color: 144A.

*Foliage description.*—Arrangement: Alternate, simple. Quantity per lateral branch: About 18. Length: About 6.25 cm. Width: About 5 cm. Shape: Pinnatifid, deeply divided. Apex: Acute. Base: Attenuate. Margin: Serrate. Texture, both surfaces: Smooth, glabrous. Venation pattern: Parallel. Petiole length: About 2.8 cm. Petiole diameter: About 4 mm. Petiole texture: Smooth.

*Color.*—Young foliage, upper surface: 137A. Young foliage, lower surface: 137B. Fully expanded foliage, upper surface: 147A; glossy. Fully expanded foliage, lower surface: 147B. Venation, upper and lower surfaces: 147B. Petiole, upper and lower surfaces: 147C.

Inflorescence description:

*Appearance.*—Single composite inflorescence form with ligulate ray florets. Inflorescences held upright on terminal and axillary peduncles. Disc and ray florets arranged acropetally on a capitulum. Inflorescences persistent. Inflorescences fragrant; faint sour smell. Inflorescences last about seven days on the plant.

*Flowering response.*—Under natural conditions, plant flower from spring to early fall; plants flower continuous during this period.

*Quantity of inflorescences.*—Very freely flowering; about 28 flower buds and inflorescences per lateral branch and more than 250 flower buds and inflorescences per plant.

*Inflorescence size.*—Diameter: About 4.5 cm. Depth (height): About 1 cm. Diameter of disc: About 1.4 cm. Receptacle diameter: About 1.4 cm. Receptacle height: About 3 mm.

*Flower buds.*—Height: About 1 cm. Diameter: About 8 mm. Shape: Roughly ovoid. Color: 73C.

*Ray florets.*—Quantity per inflorescence: About 21 arranged in one whorl. Shape: Ligulate. Length: About 2 cm. Width: About 6 mm. Apex: Emarginate. Base: Acute. Margin: Entire. Texture, upper and lower surfaces: Smooth, velvety. Aspect: Initially upright; when mature, perpendicular to the peduncle. Color: When opening, upper surface: Towards apex, 68B; towards base, 155D. When opening, lower surface: 68D. Fully opened, upper surface: Towards apex, 73B to 73D; towards base, 155D; fading to mostly 155D with 73D at apex with subsequent development. Fully opened, lower surface: 73D.

*Disc florets.*—Arrangement: Massed at the center of the inflorescence. Quantity per inflorescence: About 160. Shape: Tubular, five-parted at apex; apex, acute; base, fused. Length: About 6 mm. Diameter: At apex: About 2 mm. At base: Less than 1 mm. Color: Immature: Apex: 179A. Mid-section and base: 14B. Mature: Apex: 12A. Mid-section: 157B. Base: 157A.

*Involucral bracts.*—Appearance: Scale-like; margins, papery. Quantity per inflorescence: About 24. Length: About 3 mm. Width: About 2 mm. Shape: Elliptic. Apex: Acute. Base: Truncate. Margin: Entire. Texture, upper and lower surfaces: Glabrous, smooth. Color: Upper surface: 144C. Lower surface: 144B.

*Peduncle.*—Strength: Strong. Aspect: Upright to about 45° from vertical. Length: First peduncle: About 8.5 cm. Fourth peduncle: About 13 cm. Seventh peduncle: About 16 cm. Diameter: About 2 mm. Texture: Smooth, glabrous. Color: 144A.

*Reproductive organs.*—Androecium: Present on disc florets only. Quantity per floret: Five fused around style. Anther shape: Ovoid. Anther length: Less than 1 mm. Anther color: 14B. Amount of pollen: Scarce. Color: 14B. Gynoecium: Present on both ray and disc florets. Quantity per floret: One. Pistil length: About 6 mm. Stigma shape: Two-parted. Stigma color: 14A. Style length: About 3 mm. Style color: 144D. Ovary color: 157A. Seed/fruit: Seed and fruit production has not been observed.

Disease resistance: Resistance to pathogens common to Argyranthemum has not been observed on plants grown under commercial conditions.

Temperature/weather tolerance: Plants of the new Argyranthemum have been observed to be tolerant to rain, wind and to temperatures from −1° C. to 30° C.

I claim:

1. A new and distinct cultivar of Argyranthemum plant named 'Supamarg', as illustrated and described.

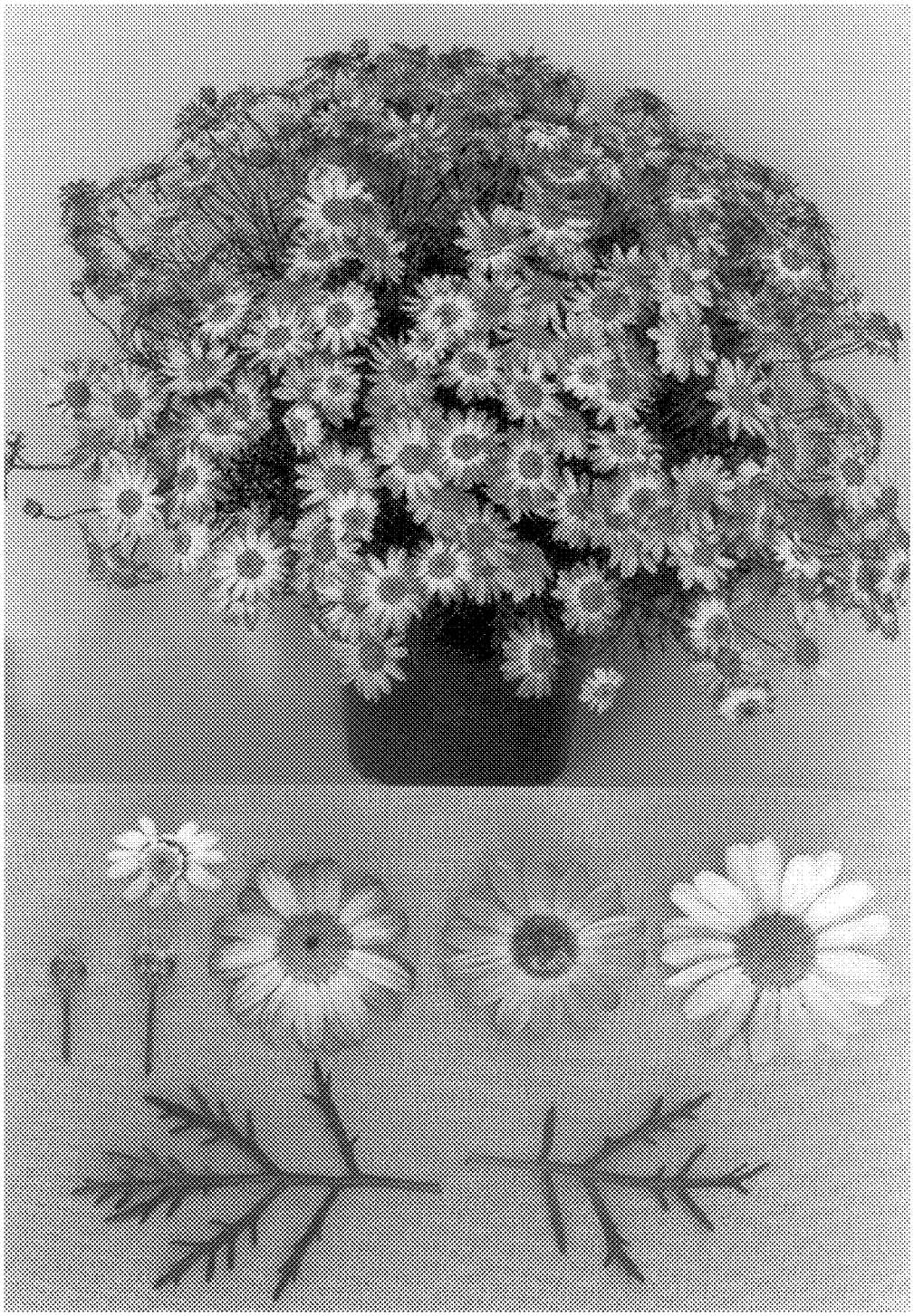

* * * * *